United States Patent [19]

Nakaji et al.

[11] 4,259,303
[45] Mar. 31, 1981

[54] METHOD OF AND SYSTEM FOR TREATING WASTE ANESTHETIC GAS

[75] Inventors: Osamu Nakaji, Sakura; Seisuke Takashima; Seishiro Nakamura, both of Kurashiki, all of Japan

[73] Assignee: Kuraray Co., Ltd., Kurashiki, Japan

[21] Appl. No.: 84,830

[22] Filed: Oct. 15, 1979

[30] Foreign Application Priority Data

Oct. 17, 1978 [JP] Japan .................................. 53-128235
Mar. 29, 1979 [JP] Japan .................................. 54-37947

[51] Int. Cl.$^3$ ............................................. B01D 53/36
[52] U.S. Cl. .................................... 423/239; 422/177; 128/203.25
[58] Field of Search ....................... 423/235, 239, 351; 128/203.25; 422/177

[56] References Cited

U.S. PATENT DOCUMENTS 2,407,221  9/1946  Bloomheart .................... 128/203.25
4,088,604  5/1978  Sermon .............................. 423/239

OTHER PUBLICATIONS

Hightower, J. W. et al. in *The Cat. Chem. of Nitrogen Oxides* Edited by R. L. Klorish; Plenum Press, N. Y. 1975, pp. 63–89.

*Primary Examiner*—G. O. Peters
*Attorney, Agent, or Firm*—Oblon, Fisher, Spivak, McClelland & Maier

[57] ABSTRACT

The present invention provides a method of treating a waste anesthetic gas by contacting the laughing gas contained in the waste anesthetic gas with a catalyst comprising one or more metal oxides selected from the group consisting of ferric oxide, cobalt oxide, cupric oxide, chromium oxide, manganese dioxide and nickel oxide to decompose the laughing gas into nitrogen and oxygen. This method is of practical value for preventing the neighborhood of hospitals from environmental pollution problem.

10 Claims, 2 Drawing Figures

4,259,303

METHOD OF AND SYSTEM FOR TREATING WASTE ANESTHETIC GAS

BACKGROUND OF THE INVENTION

1. Field of the Invention

The present invention relates to a method of and system for treating waste anesthetic gas to render the gas non-poisonous. More particularly, it relates to a method of and system for treating waste anesthetic gas to decompose the laughing gas contained in the waste anesthetic gas into a nonpoisonous gas by the action of a catalyst.

2. Description of the Prior Art

Anesthetic gases mainly used in operating rooms contain laughing gas (nitrous oxide, $N_2O$) and halothane (1,1,1-trifluoro-2-bromo-2-chloroethane). The concentration of laughing gas in anesthetic gas is so high that it reaches 50 to 75% by volume, whereas the concentration of halothane is less than 1% by volume. The rest of the gas is oxygen. The anesthetic gas after being inhaled by a patient is discharged from the anesthetic circuit as waste anesthetic gas. The composition of the thus discharged waste anesthetic gas is approximately equal to that of the fresh inhaled anesthetic gas and thus it contains a high laughing gas content as mentioned above. The detailed composition of the waste anesthetic gas to be treated by the method and system of the present invention will be described hereinafter.

It has been revealed that the health of doctors and nurses working in operating rooms is impaired by inhaling the anesthetic gas which leaks into the operating room for a long period of time. For this reason, the National Institute for Occupational Safety and Health (NIOSH) of the United States of America has advised that the anesthetic gas concentration leaking into the operating room should be less than 25 ppm for laughing gas and less than 0.5 ppm for halothane. Under these circumstances, the development of an effective countermeasure against contamination or pollution with the anesthetic gas in the operating room has attracted attention in recent years, and some hospitals are equipped with apparatus for discharging the waste anesthetic gases. Such apparatuses, are disclosed in Japanese Utility Model Publication No. 10159/1974 and Japanese Utility Model Laid-Open No. 52895/1977. In these discharge apparatuses, the waste anesthetic gas exhaled by a patient is sucked by a pump and immediately discharged out of the room without any treatment. Such a discharge or ventilation apparatus is in fact effective in reducing the concentration of anesthetic gas in the operating room. Moreover, it might cause a secondary pollution problem by spreading the polluting anesthetic gas into the neighborhood of the hospital. It is, therefore, necessary to remove the anesthetic component from the discharged anesthetic gas as far as possible or to convert the anesthetic component into nonpoisonous substances instead of discharging the waste anesthetic gas without treatment, when such waste anesthetic gas is discharged by using a discharge apparatus. Since halothane, one of the anesthetic gases, is readily adsorbed, by activated carbon, it may be relatively easily removed by providing the waste anesthetic discharge apparatus with an adsorption column filled with activated carbon or the like. An example of such apparatus is described in Japanese Utility Model Laid-Open No. 794/1974. However, no practically useful method of removing the laughing gas component is known.

SUMMARY OF THE INVENTION

An object of the present invention is, therefore, to provide a method of treating the waste anesthetic gas to render nonpoisonous the laughing gas contained in the waste anesthetic gas.

Another object of the present invention is to provide a method of treating waste anesthetic gas, which contains $N_2O$ in high concentration, to decompose the $N_2O$ for removal.

A further object of the present invention is to provide a system for treating the waste anesthetic gas to render nonpoisonous the laughing gas contained in the waste anesthetic gas.

Yet a further object of the invention is to provide a system for treating waste anesthetic gas, which contains $N_2O$ in high concentration, to decompose the $N_2O$ for removal.

Another object of the present invention is to provide a method of and apparatus applicable for decomposing and removing $N_2O$ contained in general waste gases at high concentration.

Other objects of the present invention will be made clear from the detailed description of the invention given hereinbelow.

These objects can be attained by the provision of a method of treating the waste anesthetic gas wherein the laughing gas contained in the waste anesthetic gas is contacted with a catalyst comprising of one or more metal oxides selected from the group consisting of ferric oxide, cobalt oxide, cupric oxide, chromium oxide, manganese dioxide and nickel oxide, at a temperature of from 250° C. to 650° C. to decompose the laughing gas into nitrogen and oxygen, and by the provision of a system for treating the waste anesthetic gas comprising a reactor filled with the aforementioned catalyst and provided with a heating means for heating the laughing gas to the temperature defined above.

DETAILED DESCRIPTION OF THE PREFERRED EMBODIMENTS

Figure 1:
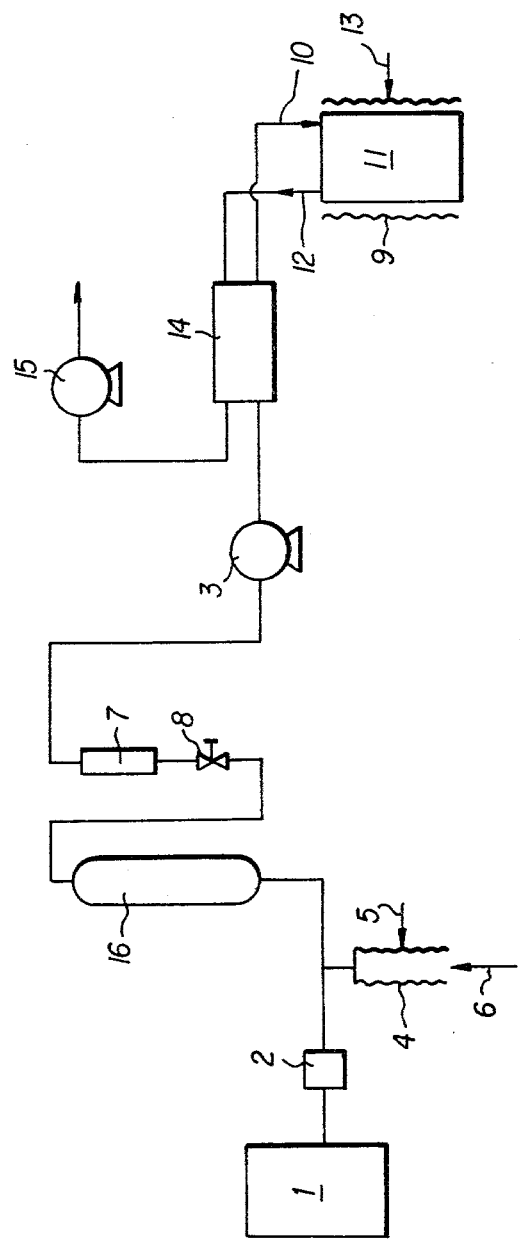
FIG. 1 is a flow sheet diagrammatically showing the system for treating waste anesthetic gas according to the present invention.

The present invention is characterized in that the laughing gas contained in the waste anesthetic gas is decomposed into oxygen and nitrogen with the use of a catalyst to become nonpoisonous. The catalyst, which may be used in the present invention, is required to have the following properties:

(a) The catalytic activity should be high enough to decompose the laughing gas into nitrogen and oxygen at a low temperature.

(b) During the decomposition of laughing gas into nitrogen and oxygen, the amount of toxic by-products such as nitrogen dioxide and nitrogen monoxide produced should be small.

(c) The catalyst should be difficult to poison by halogenated hydrocarbons including halothane commonly used as the anesthetic reagent in combination with the laughing gas.

(d) The heat resistant property thereof should be good and the usable catalyst life should be long.
(e) The catalyst should be inexpensive.

It has been found that a catalyst comprising one or more metal oxides selected from the group consisting of ferric oxide ($Fe_2O_3$), cobalt oxide (CoO), cupric oxide (CuO), chromium oxide ($Cr_2O_3$), manganese dioxide ($MnO_2$) and nickel oxide (NiO) is effectively used as that satisfying the requirements set forth above. Any of the metal oxides set forth above may not only be used singly but also may be used in the form of a binary system or a multi-component system including two or more of the compounds selected from the aforementioned group, such as the nickel oxide-chromium oxide system and cupric oxide-manganese dioxide system. Among them, the binary system catalyst composed of cupric oxide and chromium oxide is preferred, since it excellently satisfies the foregoing requirements. This binary system may be mixed with ferric oxide, nickel oxide, cobalt oxide or manganese dioxide to form a multi-component system. It has been found that a catalyst composed of cupric oxide, chromium oxide and manganese dioxide is the most suitable catalyst for decomposing laughing gas, since the catalytic activity thereof is high, small amounts of nitrogen dioxide and nitrogen monoxide are generated as the by-products, it is barely affected by the catalytic poisoning action of halothane and it has excellent heat resistant property.

In the binary catalyst composed of cupric oxide-chromium oxide, the mixing ratio of cupric oxide relative to chromium oxide is 1 to 0.1–10 (ratio by weight), and more preferably 1 to 0.2–8. If the mixing ratio is less than 0.1, the amounts of the by-product nitrogen dioxide and nitrogen monoxide tend to increase and the catalyst is likely to be poisoned by halothane. On the other hand, if the mixing ratio is in excess of 10, the catalytic activity tends to decrease. It is desirous that the quantity of the third component such as manganese dioxide as mentioned above added to the binary system composed of cupric oxide and chromium oxide be in the range of 0.05 to 20, more preferably 0.2 to 5, relative to 1 part of cupric oxide contained in the mixture of cupric oxide and chromium oxide. Within this range, the ternary catalyst acts effectively to suppress the by-product nitrogen dioxide and nitrogen monoxide and the poisonous action of halothane.

Such catalysts are known as catalysts as described above for removing $NO_x$ contained in waste gases discharged from combustion apparatuses, particularly from automobiles. (See, for example, Japanese Patent Application Laid-Open Nos. 35085/1975). The $NO_x$ pollutant is mainly composed of NO and $NO_2$, and is contained in the waste gases at the content of several thousands ppm. It has, of course, not been known that these catalysts are also effective for decomposing $N_2O$ contained in waste anesthetic gas in high concentrations of more than 10% by volume. The catalyst used in the present invention may be easily prepared by those skilled in the art in view of the disclosures of the already known literatures referred to above. Any of the metal oxides may be used in granular, spherical or powdered form, or may be supported on a carrier to increase the surface area of the catalyst. Examples of carriers used in the present invention include alumina, silica and titania. The preferred amount of each of the metal oxides supported on the carrier is 0.1 to 50% by weight (based on the carrier), particularly 1 to 30% by weight. Such a catalyst supported on the carrier may be easily prepared by applying a predetermined amount of a solution of a metal salt, such as nitrate, carbonate, acetate or oxalate, to the carrier and then heating the same to convert the metal salt into the corresponding metal oxide. The carriers may be used in various forms such as granular and spherical shapes. The binary system or multi-component system catalyst used in the present invention may be prepared merely by mixing the metal oxides, or may be prepared by mixing metal salts or metal hydroxides and then converting them into metal oxides by a conventional method.

In the present invention, the waste anesthetic gas is allowed to contact the catalyst at a temperature of 250° C. to 650° C., preferably 350° C. to 550° C. If the temperature is below 250° C., it is difficult to decompose sufficiently the laughing gas into nitrogen and oxygen. On the contrary, it is undesirous to operate the apparatus located in a hospital or the like facility at a temperature greater than 650° C. for safety's sake. It is necessary to allow the waste anesthetic gas to contact the catalyst for a reaction time of more than 0.2 second, generally for 4 to 9 seconds. The pressure in the catalytic reaction may be atmospheric pressure or above.

The treating system according to the present invention will now be described as follows. FIG. 1 is a flow sheet showing the treating system of the present invention diagrammatically. The treating system of the invention is characterized by having a reactor 9 for decomposing the laughing gas contained in the waste anesthetic gas. The waste anesthetic gas is first delivered to a discharge circuit connected with an anesthetic circuit 1 through a pop-off valve 2. The discharge circuit is provided with a blower 3 for sucking the waste anesthetic gas from the anesthetic circuit to be discharged. Such a discharge circuit is known from Japanese Utility Model Publication No. 10159/1974 and Japanese Utility Model Laid-Open No. 52895/1977 referred to hereinbefore, and is commercially available. In the present invention, the commonly used discharge circuit is used without any change. In general, there is further provided in the discharge circuit an air reservoir 4 for compensating the change in flow rate of the waste gas from the anesthetic circuit. The waste anesthetic gas is, thus, often mixed with air from the air reservoir 4, the amount of the mixed air being varied depending on the change in the flow rate of the waste gas, and then, delivered to the reactor 9 to decompose the laughing gas. As a result, the composition of the waste anesthetic gas fed into the reactor 9 varies depending on the composition of the fresh anesthetic gas supplied to a patient, the flow rate thereof and the construction of the discharge circuit. However, generally the waste anesthetic gas contains 10 to 80%, generally 20 to 50%, by volume of laughing gas, 20 to 60% by volume of oxygen, 0 to 1% by volume of halothane and the balance nitrogen and carbon dioxide. The system of the present invention may be applied to the waste gas having composition within the range as described above. The air reservoir 4 comprises, in common, a flexible elastic tube 5 provided with a suction port 6 for sucking air at the lower end thereof. The inner portion of the elastic tube constitutes a reservoir for the gas, and a large amount of gas eventually rushing out of the anesthetic circuit is once stored in the reservoir, diluted with air introduced through the suction port 6 and then delivered to the reactor 9. Further, a flow meter 7 and a flow rate control valve 8 may be provided in the discharge circuit.

The reactor 9 comprises an inlet port 10 for receiving the waste anesthetic gas from the discharge circuit, a container 11 filled with said decomposition catalyst and an outlet port 12 for discharging the decomposed gas therethrough. In the present invention, the reactor 9 is made of a material which withstands the operating temperature, and the shape and size thereof is suitably selected so that the contact time between the catalyst charged therein and the waste gas introduced therein is more than 0.2 second. For instance, a reactor comprising a cylindrical stainless steel container filled with a catalyst, and a heating means 13 for heating the introduced gas to from 250° C. to 650° C. may be used. As the heating means, various types of heaters including electric heaters may be used.

Figure 2:
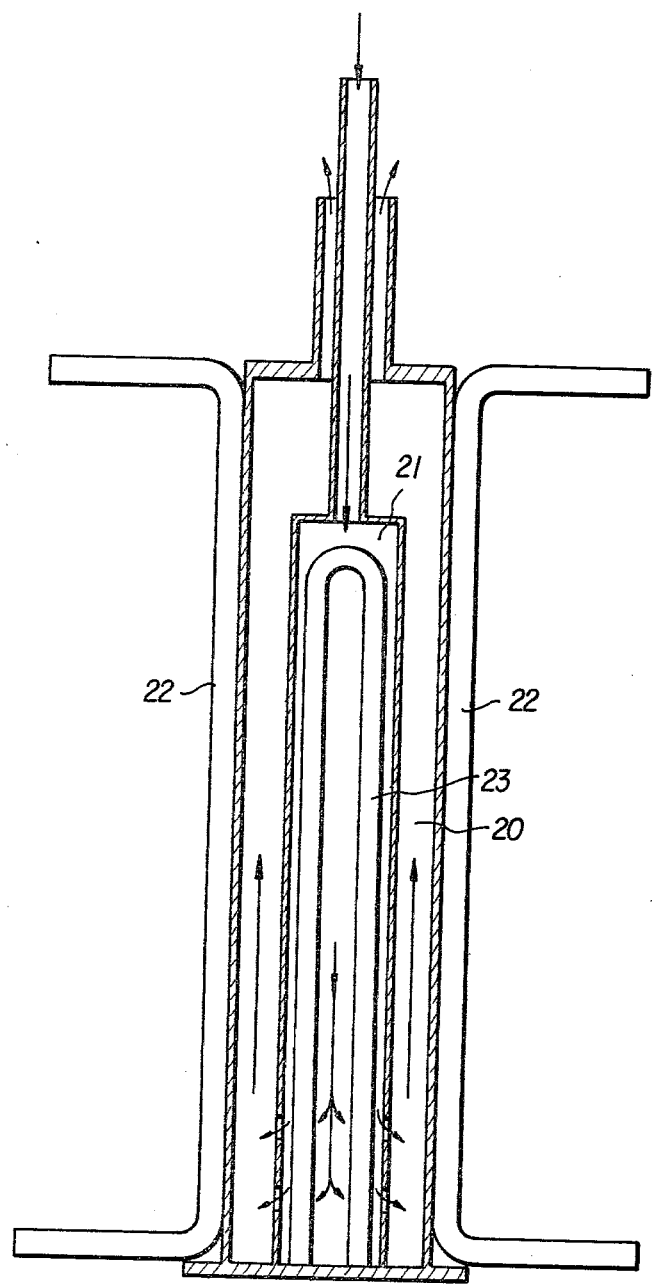
FIG. 2 is a sectional view of an embodiment of the reactor in the system for treating the waste anesthetic gas according to the present invention.

Another preferred embodiment of the reactor is shown in FIG. 2. Referring to FIG. 2, a catalyst is placed in a doughnut-shaped container 20. Since the decomposition of the laughing gas is an exothermic reaction, it is preferred to utilize the reaction heat advantageously, nevertheless heating by the heating means is necessary to initiate the reaction. In the reactor shown in FIG. 2, the waste anesthetic gas is preheated as it flows through the core portion 21 of the reactor, and is then introduced into the chamber 20 filled with the catalyst. Two heaters are positioned at the outer periphery 22 and the central portion 23.

Furthermore, in the treating system according to the present invention, a heat exchanger 14 may be incorporated, as shown in FIG. 1, to effect heat exchange between the high temperature gas discharged from the reactor and the gas introduced into the reactor in order to effectively utilize the energy. Further, in the treating system according to the present invention, a blower 15 may be provided to dilute the high temperature gas discharged from the reactor with air to be cooled thereby.

Also, in the system of the invention, it is desirous that the waste anesthetic gas discharge apparatus be provided with a canister 16 containing an activated carbon to absorb halothane for removal to decrease the amount of halothane discharged to as little as possible and to prevent the catalyst from deteriorating by the action of halothane, eventhough a catalyst which is hardly poisoned by halothane is used in the present invention. Such a canister is commercially available and may be easily procured by those skilled in the art.

It should be apparent from the foregoing description that the laughing gas component present in untreated waste anesthetic gas at high concentration in the conventional method can be fully decomposed to nonpoisonous substances in accordance with the method and system of the present invention. By the present invention, there is provided an effective countermeasure against the pollution caused by waste anesthetic gas. The most significant feature of the invention is the use of the specific catalysts defined as above, and it is surprising that such catalysts have high catalytic activity for decomposing the laughing gas component in high concentration with little by-production of NO or $NO_2$ and without being poisoned by halothane contained in the waste anesthetic gas. Many catalysts which have been known as suitable for removing $NO_x$ contained in the waste combustion gas are affected by the catalytic poisioning action of halothane, and hence are not suitable for the present invention.

The present invention will be described more specifically with reference to some examples thereof. However, it should be noted here that the scope of the present invention is not limited by such examples.

EXAMPLE 1

A spherical alumina carrier available from Mizusawa Industrial Chemicals Ltd. under the Trade name of Neobead CB (Particle Size=3 to 5 mm) was calcined at 900° C. for 3 hours and impregnated with an aqueous solution of ferric nitrate such that the amount of ferric oxide ($Fe_2O_3$) finally supported on the carrier reached 10% by weight based on the weight of the carrier, and was then heated at 600° C. for 5 hours after drying to convert ferric nitrate into ferric oxide, whereby the catalyst comprising ferric oxide supported on the carrier in an amount of 10 weight % based on the carrier was obtained.

This catalyst was charged into a stainless steel tube of 1.5 cm in internal diameter to form a catalyst bed of 10 cm in length, which was used as the reactor. This reactor was put into an electric furnace and heated to 520° C. As one composition of the waste anesthetic gas a gas mixture composed of nitrous oxide and oxygen (Nitrous Oxide:Oxygen=50:50 vol%) was employed and preheated to 520° C. by a preheater, and then fed through the inlet port of the reactor at the flow rate of 50 ml/min (the contact time of the gas mixture with the catalyst being 8.1 seconds). The gas coming out of the outlet part of the reactor was picked up and the nitrous oxide concentration thereof was determined by means of gas chromatography to be 0% by volume. This result indicated that the rate of decomposition of nitrous oxide reached 100%.

EXAMPLE 2

A spherical alumina carrier available from Mizusawa Industrial Chemicals Ltd. under the Trade Name of Neobead CB (Particle Size=3 to 5 mm) was calcined at 900° C. for 3 hours and impregnated with an aqueous solution of chromium nitrate such that the amount of chromium oxide ($Cr_2O_3$) finally supported on the carrier reached 10% by weight based on the weight of the carrier, and then heated at 600° C. for 5 hours after drying to convert chromium nitrate into chromium oxide, whereby a catalyst comprising ferric oxide supported on the carrier in an amount of 10 weight % based on the carrier was obtained. This catalyst was charged into a stainless steel tube of 1.5 cm is internal diameter to form a catalyst bed of 10 cm in length, which was used as the reactor. This reactor was put into an electric furnace and heated to 560° C. As one composition of the waste anesthetic gas a gas mixture composed of nitrous oxide and oxygen (Nitrous Oxide:Oxygen=50:50 vol%) was used and was preheated to 560° C. by a preheater. The mixture was then fed through the inlet port of the reactor at the flow rate of 50 ml/min. The gas coming out of the outlet port of the reactor was picked up and the nitrous oxide concentration thereof was determined by means of gas chromatography to be 0% by volume. This result indicated that the rate of decomposition of nitrous oxide reached 100%.

EXAMPLE 3

The same spherical alumina carrier as used in Example 1 was impregnated with an aqueous solution of cupric nitrate such that the amount of cupric oxide finally supported on the carrier reached 10% by weight based on the weight of the carrier. The supported nitrate salt was heated at 600° C. for 5 hours after drying to convert cupric nitrate into cupric oxide, whereby a catalyst comprising cupric oxide supported on the carrier in an amount of 10 weight % based on the carrier was obtained. Similarly as in Example 1, this catalyst was charged into a stainless steel tube, which was used as the reactor. The reactor was heated to 490° C., and the same gas mixture composed of nitrous oxide and oxygen which was used in Example 1, but which was preheated to 490° C. by a preheater, was passed into the inlet port of the reactor. The rate of decomposition of the laughing gas was 100%, and the total concentration of nitrogen dioxide and nitrogen monoxide contained in the gas coming out of the outlet port of the reactor was 100 ppm.

EXAMPLE 4

A spherical alumina carrier available from Mizusawa Industrial Chemicals Ltd. under the Trade Name of Neobead CB (Particle Size=3 to 5 mm) was calcined at 900° C. for 3 hours and impregnated with a mixed aqueous solution of cupric nitrate and chromium nitrate such that the amounts of cupric oxide and chromium oxide finally supported on the carrier each reached 5% by weight based on the weight of the carrier. The supported salt material was then heated at 600° C. for 5 hours after drying to convert the nitrates into the corresponding oxides, whereby a catalyst comprising cupric oxide and chromium oxide supported on the carrier each in an amount of 5 weight % based on the carrier was obtained. This catalyst was charged into a stainless steel tube of 1.5 cm in internal diameter to form a catalyst bed of 10 cm in length, which was used as the rector. This reactor was placed into an electric furnace and heated to 500° C. As one composition of the waste anesthetic gas a gas mixture composed of nitrous oxide and oxygen (Nitrous Oxide:Oxygen=50:50 vol%) was preheated to 500° C. by a preheater, and then the gas was fed through the inlet port of the reactor at the flow rate of 50 ml/min (the contact time of the gas mixture with the catalyst being 8.1 seconds). The gas coming out of the outlet port of the reactor was picked up and the nitrous oxide concentration thereof was determined by means of gas chromatography to be 0% by volume. This result indicated that the rate of decomposition of nitrous oxide reached 100%. The total concentration of nitrogen dioxide and nitrogen monoxide contained in the gas coming out of the outlet port of the reactor was 32 ppm.

EXAMPLE 5

Similarly, following the general procedure of Example 4, a catalyst comprising nickel oxide, cupric oxide and chromium oxide supported on a spherical alumina carrier in amounts of 13%, 7% and 2% by weight, respectively, based on the carrier was obtained. This catalyst was charged in a stainless steel tube similarly as in Example 4 to prepare the reactor which was then heated to 480° C. The same gas mixture composed of nitrous oxide and oxygen as used in Example 4 was preheated to 480° C. by a preheater, and then was fed through the inlet port of the reactor similarly as in Example 1. The rate of decomposition of the laughing gas was 100%, and the total concentration of nitrogen dioxide and nitrogen monoxide contained in the gas coming out of the outlet port of the reactor was 5 ppm. When 750 mg of halothane was added to the gas mixture composed of nitrous oxide and oxygen during the reaction time in the form of vapor, the rate of decomposition of nitrous oxide was slightly reduced from 100% to 97%. As will be clear from the foregoing, this catalyst had high catalytic activity, formed little nitrogen dioxide and nitrogen monoxide and was only slightly affected by the catalytic poisoning action of halothane.

EXAMPLE 6

A spherical titania carrier (available from Mizusawa Industrial Chemicals Ltd., Particle Size=3 to 5 mm) was impregnated with a mixed aqueous solution of cobalt nitrate and manganese nitrate such that the amount of cobalt oxide finally supported on the carrier reached 7% by weight and the amount of manganese dioxide finally supported on the carrier reached 3% by weight (based on the weight of the carrier). The supported salt material was heated at 600° C. for 6 hours after drying to convert the nitrates into the corresponding oxides, whereby a catalyst containing 7% by weight of cobalt oxide and 3% by weight of manganese dioxide supported on the carrier was obtained. This catalyst was charged in a stainless steel tube similarly as in Example 4 to prepare the reactor which was heated to 490° C., and then fed with a gas mixture composed of nitrous oxide and oxygen through the inlet port of the reactor. The rate of decomposition of nitrous oxide was 100%, and the total concentration of nitrogen dioxide and nitrogen monoxide contained in the gas coming out of the outlet port of the reactor was 8 ppm.

EXAMPLE 7

Following the general procedure of Example 4, a catalyst comprising 6% by weight of cupric oxide, 6% by weight of chromium oxide and 1% by weight of manganese dioxide supported on a spherical alumina carrier (% by weight being based on the carrier) was obtained. This catalyst was charged in a stainless steel tube similarly as in Example 4 to prepare the reactor which was heated to 480° C. The same gas mixture composed of nitrous oxide and oxygen as used in Example 4 was preheated to 480° C. by a preheater, and then fed through the inlet port of the reactor similarly was in Example 4. The rate of decomposition of nitrous oxide was 100%, and the total concentration of nitrogen dioxide and nitrogen monoxide contained in the gas coming out of the outlet port of the reactor was 22 ppm. When 750 mg of halothane was added to the gas mixture composed of nitrous oxide and oxygen during the reaction in the form of vapor, the rate of decomposition of nitrous oxide was slightly reduced from 100% to 99%. Also, when this catalyst was subjected to heating treatment at 900° C. for 3 hours and a similar experiment was repeated using the thus treated catalyst, neither the rate of decomposition of the laughing gas nor the total concentration of nitrogen dioxide and nitrogen monoxide was changed. As such, this catalyst had high catalytic activity, formed only little nitrogen dioxide and nirtrogen monoxide, was slightly affected by the catalytic poisoning action of halothane and was excellent in heat resistant property.

EXAMPLE 8

Similarly, following the general procedure of Example 4, a catalyst of 5% by weight of cupric oxide, 5% by weight of chromium oxide and 3% by weight of manganese dioxide supported on a spherical alumina carrier (% by weight being based on the carrier) was obtained. This catalyst was charged in a stainless steel tube of 8 cm in internal diameter to form a catalyst bed of 75 cm in length, which was used as the reactor. This reactor was heated to 540° C. by an electric heater, and was fed with a gas mixture composed of nitrous oxide and air (Laughing Gas:Air=27:74 vol%) at the flow rate of 15 l/min through the inlet port of the reactor (Temperature of the Gas: 470° C. to 550° C). The rate of decomposition of nitrous oxide was 98%, and the total concentration of nitrogen dioxide and nitrogen monoxide contained in the gas coming out of the outlet port of the reactor was 6 ppm. The reaction time of one cycle of this experiment was about 3 hours. No suggestion of a reduction in decomposition rate of nitrous oxide was observed even after the reaction cycles had been repeated for about 50 hours.

What is claimed is:

1. A method of treating waste anesthetic gas containing laughing gas ($N_2O$), comprising:
    passing said waste anesthetic gas over a catalyst comprising at least one metal oxide selected from the group consisting of ferric oxide, cobalt oxide, cupric oxide, chromium oxide, manganese dioxide and nickel oxide at a temperature of 250° C. to 650° C. to decompose said laughing gas to nitrogen and oxygen.

2. The method of claim 1, wherein said catalyst is supported on a carrier selected from the group consisting of alumina, silica and titania.

3. The method of claim 1 or 2, wherein said catalyst is a binary system catalyst comprising cupric oxide and chromium oxide, the mixing ratio by weight of cupric oxide/chromium oxide being 1/0.1–10.

4. The method of claim 3, wherein said catalyst is a ternary system catalyst comprising cupric oxide, chromium oxide and manganese dioxide, the mixing ratio by weight of cupric oxide/chromium oxide/manganese oxide being 1/0.1–10/0.05–20.

5. The method of claim 1, wherein said metal oxide catalyst is supported on a carrier in an amount of 0.1 to 50% by wt. based on said carrier.

6. The method of claim 1, wherein said temperature of decomposition ranges from 350° C. to 550° C.

7. A system for treating a waste anesthetic gas, comprising:
    a discharge circuit for removing the waste anesthetic gas from an anesthetic circuit connected to a reactor, said reactor comprising:
    (a) an inlet port for receiving the waste anesthetic gas from said discharge circuit,
    (b) a container filled with a catalyst comprising at least one metal oxide selected from the group consisting of ferric oxide, cobalt oxide, cupric oxide, chromium oxide, manganese dioxide and nickel oxide for decomposing the laughing gas present in said waste anesthetic gas, said container being provided with a heating means for heating the laughing gas at a temperature of 250° C. to 650° C., and
    (c) an outlet port for discharging the decomposed gas therethrough.

8. The system of claim 7, wherein said catalyst is supported on a carrier selected from the group consisting of alumina, silica and titania.

9. The system of claim 7 or 8, wherein said catalyst is a binary system catalyst comprising cupric oxide and chronium oxide, the mixing ratio by weight of cupric oxide/chromium oxide being 1/0.1–10.

10. The system of claim 7 or 8, wherein said catalyst is a ternary system catalyst comprising cupric oxide, chromium oxide and manganese dioxide, the mixing ratio by weight of cupric oxide/chromium oxide/manganese oxide being 1/0.1–10/0.05–20.

* * * * *

UNITED STATES PATENT AND TRADEMARK OFFICE
CERTIFICATE OF CORRECTION

PATENT NO. : 4,259,303
DATED : March 31, 1981
INVENTOR(S) : OSAMU NAKAJI ET AL

It is certified that error appears in the above—identified patent and that said Letters Patent is hereby corrected as shown below:

Column 1, Line 39: delete "Unde" and insert --Under--.

Column 5, Line 41: delete "absorb" and insert --adsorb--.

Column 7, Lines 32 to 33: delete "rec-tor" and insert --reactor--.

Signed and Sealed this

First Day of December 1981

[SEAL]

Attest:

Attesting Officer

GERALD J. MOSSINGHOFF
Commissioner of Patents and Trademarks